US012564689B2

(12) United States Patent
Zolotukhin

(10) Patent No.: US 12,564,689 B2
(45) Date of Patent: Mar. 3, 2026

(54) INJECTION DEVICE AND COMPONENTS THEREOF

(71) Applicants: PULSE NEEDLEFREE SYSTEMS, INC., Lenexa, KS (US); OTSUKA PHARMACEUTICAL CO., LTD., Tokyo (JP)

(72) Inventor: Mikhail Zolotukhin, Shawnee, KS (US)

(73) Assignee: PULSE NEEDLEFREE SYSTEMS, INC., Lenexa, KS (US)

( * ) Notice: Subject to any disclaimer, the term of this patent is extended or adjusted under 35 U.S.C. 154(b) by 1197 days.

(21) Appl. No.: 17/442,396

(22) PCT Filed: Apr. 15, 2020

(86) PCT No.: PCT/US2020/028172
§ 371 (c)(1),
(2) Date: Sep. 23, 2021

(87) PCT Pub. No.: WO2020/214621
PCT Pub. Date: Nov. 22, 2020

(65) Prior Publication Data
US 2022/0167607 A1 Jun. 2, 2022

Related U.S. Application Data

(60) Provisional application No. 62/835,700, filed on Apr. 18, 2019.

(51) Int. Cl.
*A61M 5/46* (2006.01)
*A01M 21/04* (2006.01)
(Continued)

(52) U.S. Cl.
CPC ............ *A61M 5/46* (2013.01); *A01M 21/043* (2013.01); *A61D 7/00* (2013.01); *A61M 5/204* (2013.01);
(Continued)

(58) Field of Classification Search
CPC ...... A61M 5/46; A61M 5/204; A61M 5/3293; A61M 5/345; A61M 5/347; A61M 5/20;
(Continued)

(56) References Cited

U.S. PATENT DOCUMENTS

| | | |
|---|---|---|
| 1,217,630 A | 2/1917 | Powers |
| 1,520,508 A | 12/1924 | Platt et al. |

(Continued)

FOREIGN PATENT DOCUMENTS

| | | |
|---|---|---|
| CL | 68802 A1 | 3/2024 |
| CN | 201107995 A | 9/2008 |

(Continued)

OTHER PUBLICATIONS

Article, "Natural cocktail used to prevent, treat disease of wine grapes", AgriLife Today, Aug. 4, 2015, downloaded from the internet on Dec. 17, 2021 at https://agrilifetoday.tamu.edu/2015/08/04/natural-cocktail-used-to-prevent-treat-disease-of-wine-grapes/ (4 pgs).

(Continued)

*Primary Examiner* — Tasnim Mehjabin Ahmed
(74) *Attorney, Agent, or Firm* — STINSON LLP

(57) ABSTRACT

The present invention is directed to a needle retention assembly, an injectate delivery system, a needle, and a safety mechanism, all of which are for use with an injection device. The needle retention assembly includes a needle offset nut which is configured to removably attach to a needle retention nut and to provide support to the needle. The injectate delivery system includes an injectate holding compartment, (Continued)

a plunger, and a resilient member. The needle has a sidewall defining a longitudinal channel and includes at least two orifices in the sidewall, but does not include an orifice at a tip of the needle. The safety mechanism includes a dual switch that includes two switch elements that are each positioned on opposing sides of a handle of the injection device.

12 Claims, 11 Drawing Sheets

(51) Int. Cl.

| | | |
|---|---|---|
| *A61D 7/00* | (2006.01) | |
| *A61M 5/20* | (2006.01) | |
| *A61M 5/32* | (2006.01) | |
| *A61M 5/34* | (2006.01) | |

(52) U.S. Cl.
CPC ........ *A61M 5/3291* (2013.01); *A61M 5/3293* (2013.01); *A61M 5/345* (2013.01); *A61M 5/347* (2013.01); *A61M 5/20* (2013.01); *A61M 5/3286* (2013.01); *A61M 2207/00* (2013.01)

(58) Field of Classification Search
CPC .............. A61M 5/3286; A61M 5/3291; A61M 2207/00; A01M 21/043
See application file for complete search history.

(56) References Cited

U.S. PATENT DOCUMENTS

| | | | |
|---|---|---|---|
| 2,517,689 | A | 8/1950 | Lement |
| 3,063,450 | A | 11/1962 | Simon et al. |
| 5,069,225 | A | 12/1991 | Okamura |
| 5,287,992 | A | 2/1994 | Merving |
| 5,921,966 | A | 7/1999 | Bendek et al. |
| 6,413,236 | B1 | 7/2002 | Van Dyke |
| 6,524,276 | B1 | 2/2003 | Halseth et al. |
| 6,565,538 | B2 | 5/2003 | Quinn et al. |
| 7,513,887 | B2 | 4/2009 | Halseth et al. |
| 8,034,033 | B2 | 10/2011 | Grinberg |
| RE43,141 | E | 1/2012 | Halseth et al. |
| 8,167,837 | B2 | 5/2012 | Judd et al. |
| 8,394,061 | B2 | 3/2013 | Kazemzadeh |
| 9,901,682 | B2 | 2/2018 | Grinberg |
| 2003/0144633 | A1 | 7/2003 | Kirchhofer |
| 2004/0079169 | A1 | 4/2004 | Wild et al. |
| 2007/0228185 | A1 | 10/2007 | Matsumoto |
| 2010/0191184 | A1 | 7/2010 | Choi |
| 2010/0280460 | A1* | 11/2010 | Markussen .......... A61M 5/322 604/195 |
| 2011/0295204 | A1 | 12/2011 | Bang |
| 2015/0209571 | A1 | 7/2015 | Raidt et al. |
| 2017/0239425 | A1 | 8/2017 | Castanon et al. |
| 2017/0368267 | A1 | 12/2017 | Woloschuk et al. |
| 2018/0117260 | A1 | 5/2018 | Shluzas et al. |
| 2018/0117261 | A1 | 5/2018 | Steese-Bradley et al. |
| 2018/0133408 | A1 | 5/2018 | Shluzas et al. |
| 2018/0161518 | A1 | 6/2018 | Shluzas et al. |
| 2018/0207365 | A1 | 7/2018 | Grinberg |

FOREIGN PATENT DOCUMENTS

| | | | |
|---|---|---|---|
| CN | 102725014 | A | 10/2012 |
| CN | 205460432 | U | 8/2016 |
| CN | 208175468 | U | 12/2018 |
| CN | 212034989 | U | 12/2020 |
| EP | 1291029 | A1 | 3/2003 |
| FR | 3052635 | A1 | 12/2017 |
| GB | 978570 | A | 12/1964 |
| JP | 2010193802 | A | 9/2010 |
| KR | 20110018626 | A | 2/2011 |
| SG | 132148 | A1 | 6/2007 |
| WO | 2011125475 | A1 | 10/2011 |
| WO | 2012029082 | A1 | 3/2012 |
| WO | 2015110535 | A1 | 7/2015 |
| WO | WO 2016065484 | A1 | 5/2016 |
| WO | WO 2016115628 | A1 | 7/2016 |
| WO | WO 2018085451 | A1 | 5/2018 |
| WO | WO 2018085458 | A1 | 5/2018 |
| WO | WO 2018085462 | A1 | 5/2018 |
| WO | 2020021041 | | 1/2020 |

OTHER PUBLICATIONS

International Search Report and Written Opinion dated Aug. 7, 2020 for related PCT Application PCT/US2020/028172 filed on Apr. 15, 2020 (14 pgs).

\* cited by examiner

INJECTION DEVICE AND COMPONENTS THEREOF

CROSS-REFERENCE TO RELATED APPLICATIONS

This application is based on and claims priority to U.S. Provisional Application Ser. No. 62/835,700 filed on Apr. 18, 2019, which is hereby incorporated herein by reference.

BACKGROUND OF THE INVENTION

1. Field of the Invention

The present invention relates to the field of injection devices.

2. Description of Related Art

Historically, plant pests and diseases have been controlled by mass application of pesticides. However, many pesticides contain nicotine. Nicotine-based pesticides have been shown to be a cause in the decline of bee populations and are being restricted in certain jurisdictions. Concerns over the environmental and health impacts of conventional pesticides have led to the research and development of more natural pesticides or biocontrol measures that are delivered to the plant in small doses via injection.

In developing alternatives to mass application of conventional pesticides for the control of plant bacteria, researchers have developed virulent bacteriophages that serve as biocontrol agents for diseases. One such disease is Pierce's Disease, which impacts grapevines and other plants, and is spread plant to plant via insects. While conventional pesticides were used to control the insects that transmit plant disease between plants, bacteriophages seek to limit the impact of the bacteria once the bacteria is present within the plant. Unlike conventional pesticides, however, bacteriophages cannot effectively be applied to the surface of the plant and must instead be injected into the plant to be effective.

When injecting vascular plants for certain applications, such as bacteriophages, it is desirable to deliver the injectate into the xylem of the plant. Xylem is plant vascular tissue that transports water and nutrients from the plant's roots to its stems and leaves. As such, injections into the xylem can allow the injectate to be transported and exposed, via the xylem's natural pathways, to a large portion of the plant's tissues. Injections into the xylem may also be desirable when the injectate is intended to affect bacteria that are present in the plant's xylem tissues. Known applications for injections into the xylem tissue are prophylactics and treatments related to the plant pathogen bacteria *Xylella fastidiosa* and *Xanthomonas*, commonly known as Pierce's Disease in viticulture.

In attempting to inject liquid into the xylem of grapevines, several technical challenges are presented. First, in plants of varying ages and sizes, xylem tissue is found in different depths beneath the outside of the plant. For example, in a young vine, the xylem tissue may be found 1-2 millimeters into the vine. In more mature vines, the xylem tissue may be found 3-4 millimeters into the vine. So, a uniform injection method is not possible for different types and/or ages of vines. In addition, without pressurized supply of injectate, the injectate may only be exposed to a small portion of the xylem. Moreover, when delivering very small dose volumes (<200 microliters), it is difficult to fully prime the injection device such that each cycle of the injection device released the desired dose volume to be administered. The small dose volumes and narrow pathways of the fluid path can make the injection device priming process challenging. Relatedly, when a medicine vial is mounted on the injection device, it is often challenging to deliver injections in positions where the medicine vial may be positioned at an angle that does not feed the injectate into the device by gravity. Injection devices that rely upon gravity to pressurize the injectate supply are not ideal. Additionally, needles of injection devices may become bent or broken due to the stiffness of the vines, and it can be difficult to replace the needles while working in the vineyard and with limited access to special tools.

BRIEF SUMMARY OF THE INVENTION

In one aspect, the present invention is directed to a needle retention assembly for use with an injection device. The injection device includes a needle retention nut and a needle offset nut. The needle retention nut is configured to removably attach to the injection device and to removably secure a needle to the injection device. The needle offset nut is configured to removably attach to the needle retention nut and to provide support to the needle.

In certain embodiments, the needle retention nut and the needle offset nut include any suitable offset engagement mechanisms that allow the needle retention nut to be independent separated from the needle offset nut and the injection device. Suitable offset engagement mechanisms include, but are not limited to, threads, flange and flange engagement structures, pin-locks, ball-locks, key-locks, and combinations thereof. Preferably, the needle retention nut is removably attachable to the injection device via rotational engagement. Preferably, the needle offset nut is removably attachable to the needle retention nut via rotational engagement. More preferably, the needle retention nut is removably attachable to the injection device via rotational engagement in a first rotational direction, and the needle offset nut is removably attachable to the needle retention nut via rotational engagement in a second rotational direction that is opposite the first rotational direction.

In certain embodiments, the needle retention nut includes a retention nut opening for receiving a proximal portion of the needle. The needle retention nut opening is defined by a retention nut opening inner wall. The needle retention nut is removably attached to the injection device and the needle is removably secured to the injection device. The proximal portion of the needle is positioned within the retention nut opening, and a diameter of the proximal portion of the needle is smaller than a diameter of the retention nut opening.

In certain embodiments, the needle offset nut includes an offset nut channel for receiving a distal portion of the needle. The offset nut channel is defined by an offset nut channel inner wall. When the needle offset nut is removably attached to the needle retention nut, the distal portion of the needle is positioned within the offset nut channel. Preferably, a diameter of the offset nut channel is larger than an outer diameter of the distal portion of the needle, and the offset nut channel inner wall of the offset nut channel is in abutting engagement with a side wall of a distal portion of the needle when the needle is removably secured to the injection device by the needle retention nut.

In another aspect, the present invention is directed to a method of attaching a needle to an injection device with the needle retention assembly of the present invention. The method includes: positioning the proximal portion of the needle within the retention nut opening of the needle retention nut; attaching the needle retention nut to the injection device; and positioning the offset nut channel of the needle offset nut over a distal portion of the needle; and attaching the needle offset nut to the needle retention nut.

In still another aspect, the present invention is directed to a method of removing a needle from an injection device that includes the needle retention assembly of the present invention. The method includes: detaching the needle retention nut from the injection device; and removing the needle from the retention nut opening of the needle retention nut. In certain embodiments, the method further includes detaching the needle offset nut from the needle retention nut. Preferably, the needle offset nut is detached from the needle retention nut prior to detaching the needle retention nut from the injection device.

In yet another aspect, the present invention is directed to an injectate delivery system for use with an injection device. The injectate delivery system includes an injectate holding compartment, a plunger, and a resilient member. The plunger is slidably positionable within the injectate holding compartment to form a fluid tight seal with an inner wall of the injectate holding compartment. When the injectate holding compartment is attached to the injection device, it is in fluid communication with a dose chamber of the injection device. The resilient member is configured to apply continuous pressure to the plunger, thereby forcing an injectate from the injectate holding compartment to the dose chamber when the injectate holding compartment is attached to the injection device such that neither gravity nor negative pressure are required to prime the dose chamber.

In certain embodiments, the resilient member is a spring.

In still one more aspect, the present invention is directed to a method of using the injectate delivery system of the present invention. The method includes: pressing a tip of a needle into a subject to be injected, and injecting an injectate into the subject to be injected. The needle is positioned for use in the injection device and the injectate delivery system is attached to the injection device. The injectate is supplied to the dose chamber from the injectate holding compartment. The resilient member applies continuous pressure to the plunger such that neither gravity nor negative pressure are required to prime the dose chamber. Movement of the plunger toward an end of the injectate holding compartment forces the injectate from the injectate holding compartment to the dose chamber.

In still another aspect, the present invention is directed to a needle for use with an injection device. The needle has a sidewall defining a longitudinal channel. The needle includes at least two orifices on a sidewall of the needle.

In yet one more aspect, the present invention is directed to a safety mechanism for use with an injection device that includes a dual switch that includes two switch elements that are each positioned on opposing sides of a handle of the injection device. The dual switch is movable between an on and an off position, and movement of the switch element on one side of the dual switch automatically moves the switch element on the opposite side of the handle.

In still one more aspect, the present invention is directed to an injection device that includes one or more of the following: the needle retention assembly of the present invention; the injectate delivery system of the present invention; the needle of the present invention; and the safety mechanism of the present invention.

In certain embodiments, at least one of the switch elements includes a depressible button, and the dual switch is movable between the on and the off positions by simultaneously depressing the button and moving either switch element between the on and the off position.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 11 is a side view of the needle shown in FIG. 1.

DETAILED DESCRIPTION OF PREFERRED EMBODIMENT

Figure 1:
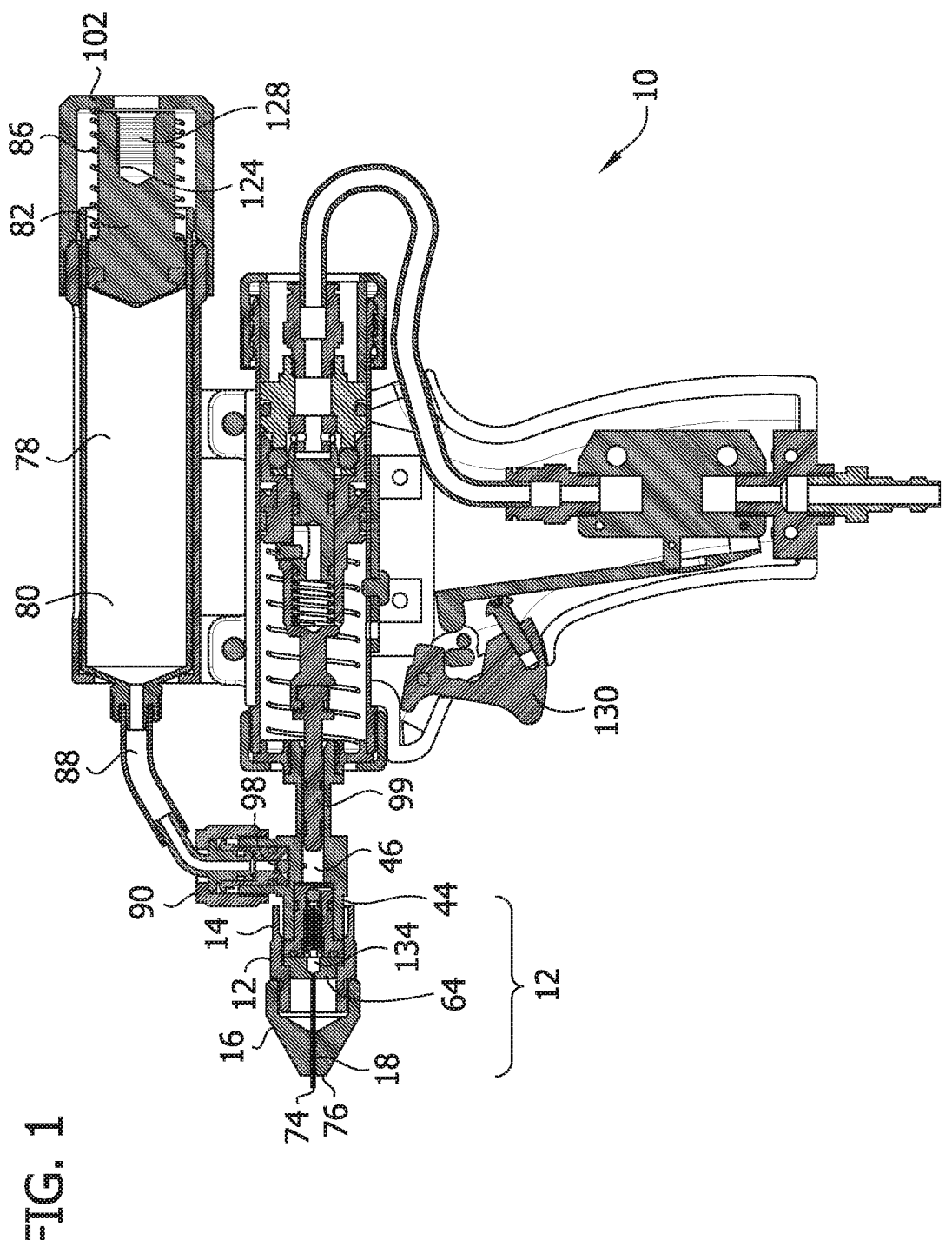
FIG. 1 is a cross-sectional view of an exemplary injection device of the present invention.

Certain aspects of the invention will now be described with respect to the exemplary embodiments depicted in the figures, but are not limited to such embodiments. FIG. 1 depicts an exemplary embodiment of an injection device 10 of the present invention.

In one aspect, the present invention is directed to a needle retention assembly 12. Needle retention assembly 12 is configured to provide support to a needle used with an injection device, set the penetration depth of the needle used with an injection device, and allow for easier and safer removal of the needle, especially when needle is broken, bent, and/or damaged.

Figure 2:
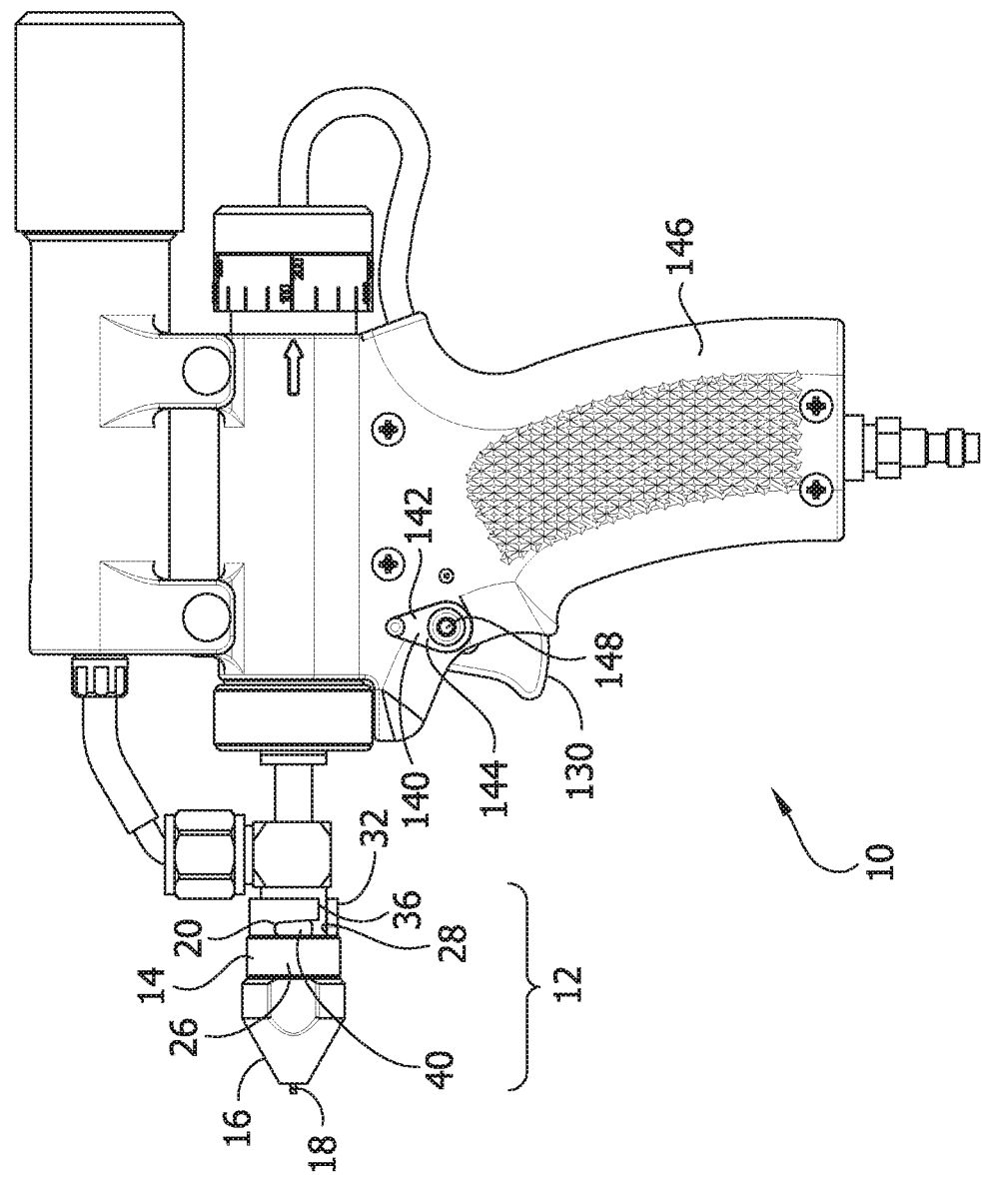
FIG. 2 is a side view of the injection device of FIG. 1 with the safety mechanism in the off position
Figure 3:
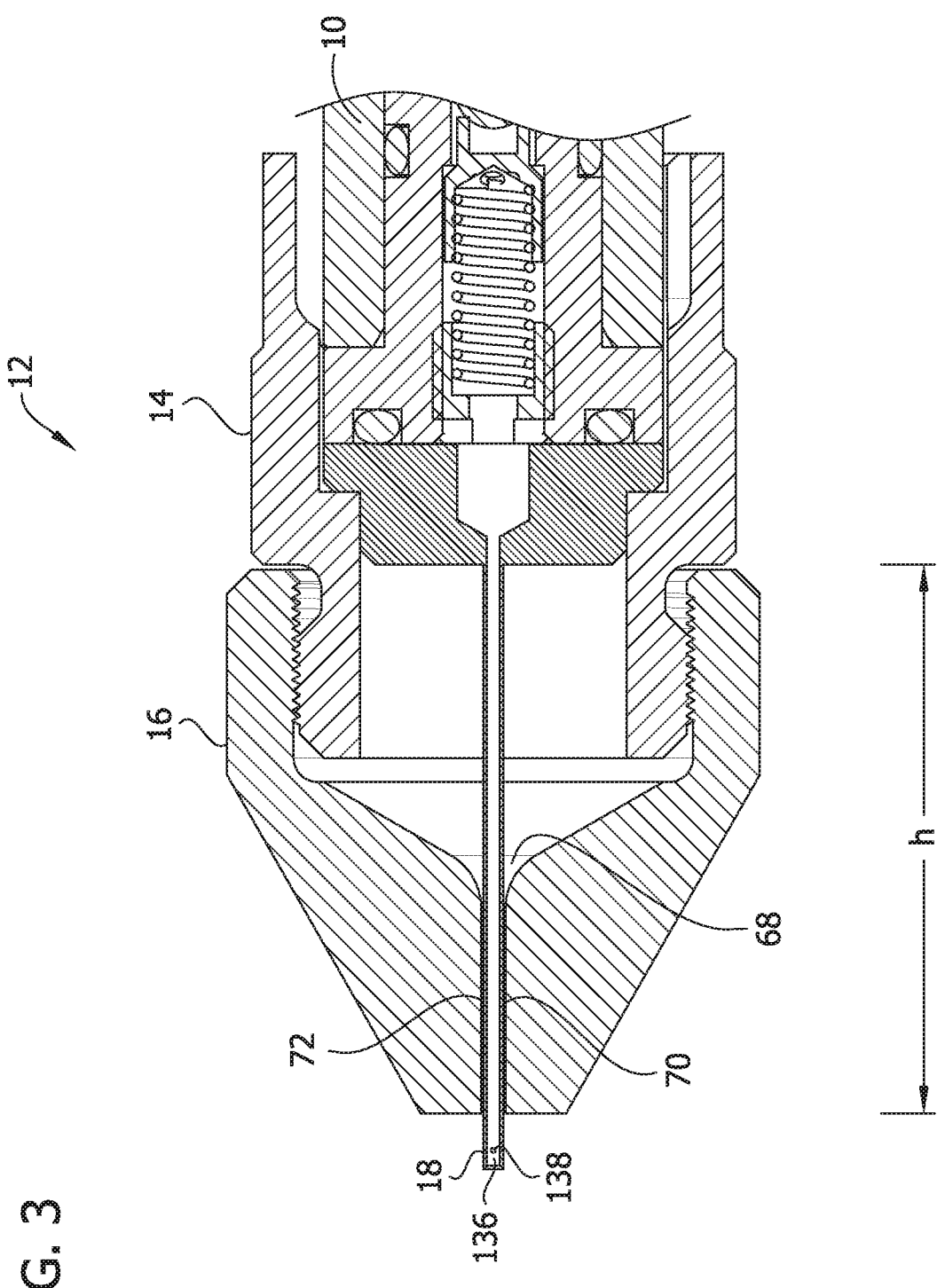
FIG. 3 is a partial cross-sectional view of the injection device of FIG. 1 showing the needle retention assembly.
Figure 4:
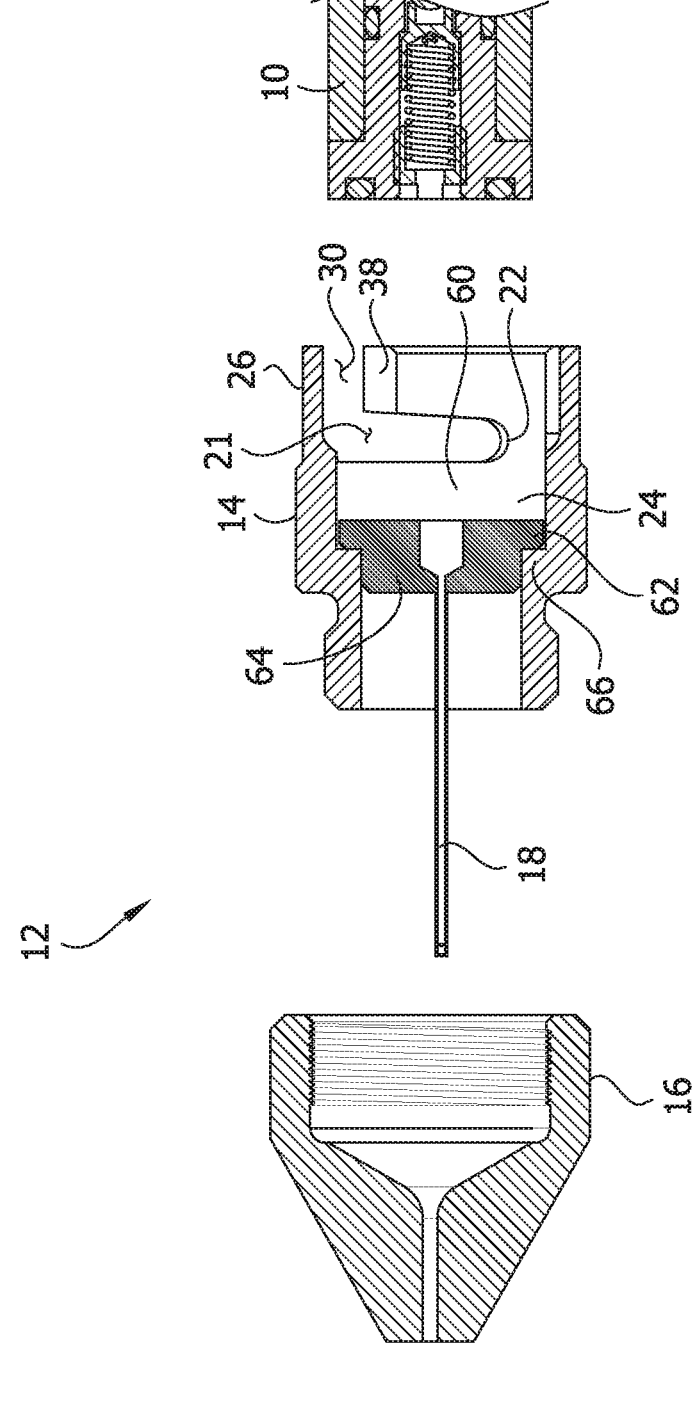
FIG. 4 is a partial cross-sectional view of the injection device of FIG. 1, showing the needle retention assembly, wherein the needle offset nut and the needle retention nut are detached from the injection device.
Figure 5:
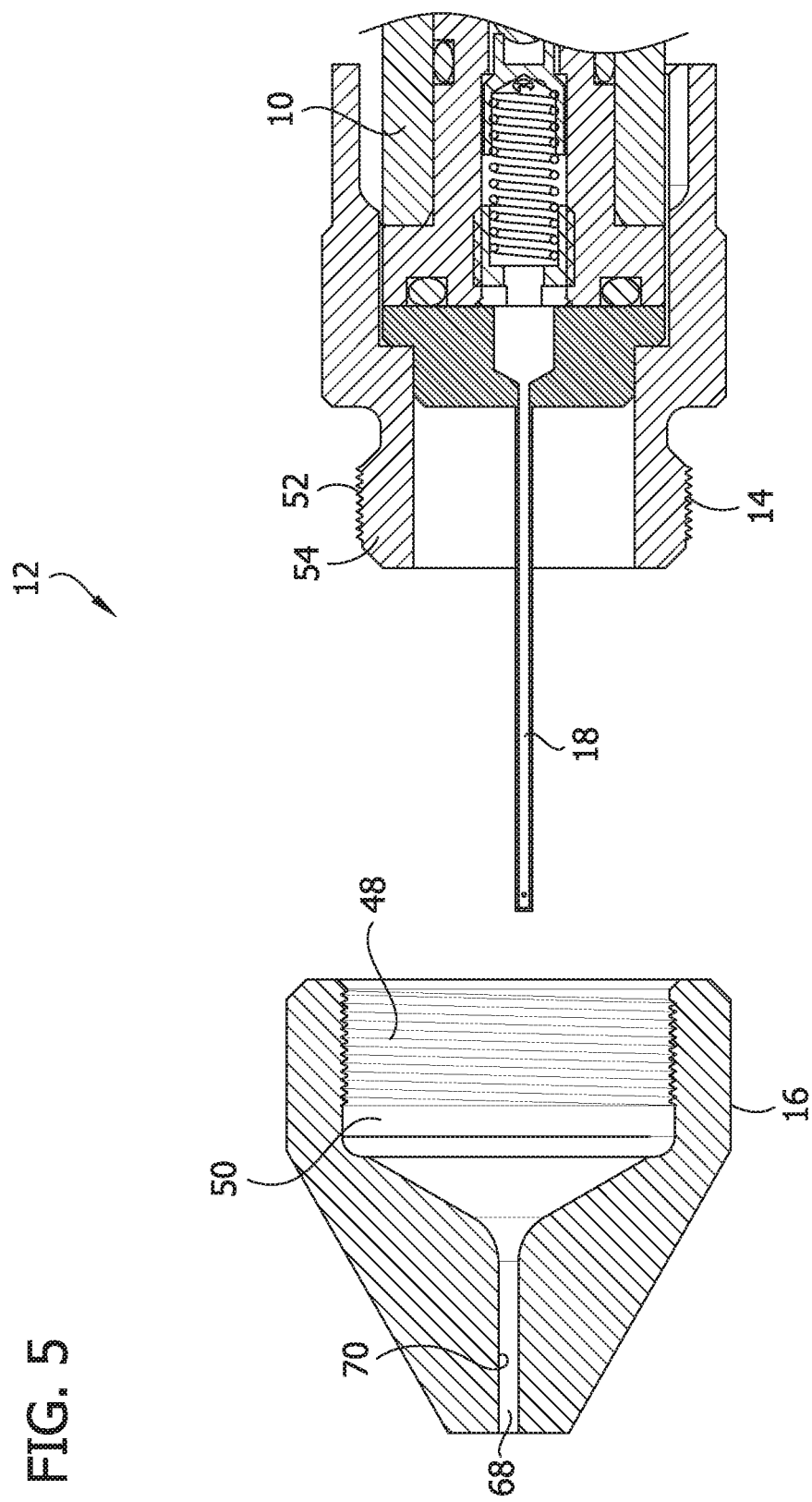
FIG. 5 is a partial cross-sectional view of the injection device of FIG. 1, showing the needle retention assembly, wherein the needle offset nut is detached from the needle retention nut.

Referring to FIG. 2, needle retention assembly 12 includes cylindrical needle retention nut 14 and semi-conical needle offset nut 16. Referring to FIGS. 3 and 4, needle retention nut 14 is configured to removably attach to injection device 10 and to removably secure needle 18 to injection device 10. As shown in FIGS. 3 and 5, needle offset nut 16 is configured to removably attach to needle retention nut 14 and to provide support to needle 18. Needle retention nut

14 may be removably attachable to injection device 10 via rotational engagement, and needle offset nut 16 may be removably attachable to needle retention nut 14 via rotational engagement.

In certain embodiments, needle retention nut 14 may be removably attachable to injection device 10 in via rotational engagement in a first rotational direction, and needle offset nut 16 may be removably attachable to needle retention nut 14 via rotational engagement in a second rotational direction that is opposite the first rotational direction; this configuration enables easier detachment of needle offset nut 16 from needle retention nut 14 without simultaneous and potentially undesirable detachment of needle retention nut 14 from injection device 10.

Figure 6:
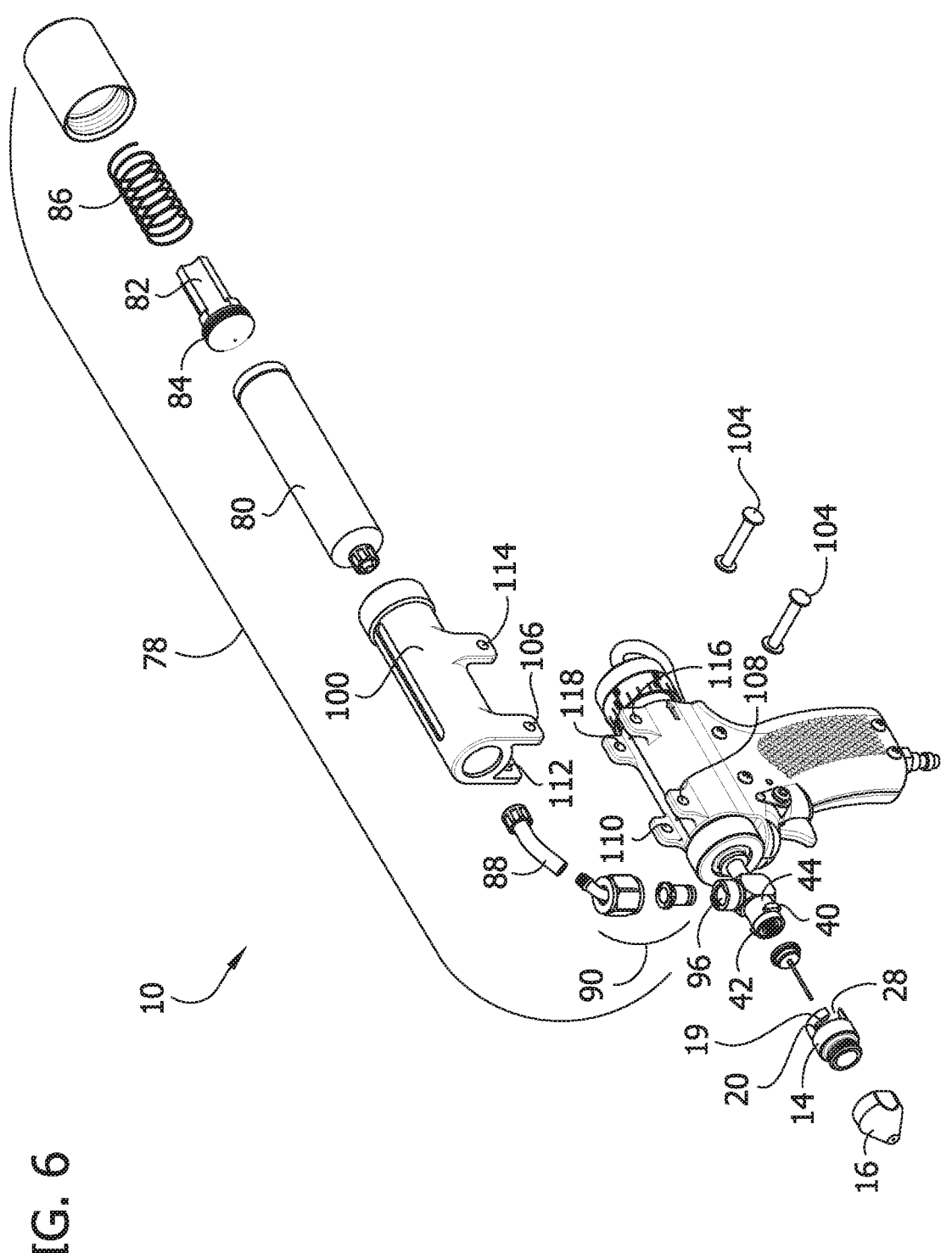
FIG. 6 is an exploded view of the injection device of FIG. 1.

As shown in FIGS. 2, 4, and 6, needle retention nut 14 includes two tapered radial grooves 19, 21 that are each defined by arcuate radial sidewalls 20, 22 positioned opposite one another that each extend between needle retention nut inner cylindrical wall 24 and needle retention nut outer cylindrical wall 26 of needle retention nut 14. Needle retention nut 14 also includes two alignment openings 28, 30 positioned opposite one another that are each defined by respective first axial sidewall 32 and second axial sidewall 36, and corresponding opposite first axial sidewall and second axial sidewalls 38 and that each extend between inner cylindrical wall 24 and outer cylindrical wall 26 of needle retention nut 14. Radial grooves 19 and 21 are each oriented in opposite directions. Alignment openings 28, 30 are configured to align with two identical flanges 40 (shown in FIGS. 2 and 6), 42 (partially shown in FIG. 6) on injection device 10 in order to position needle retention nut 14 for securement to injection device 10, and arcuate sidewalls 20, 22 of radial grooves 19, 21 are each configured to secure needle retention nut 14 to injection device 10 by rotationally engaging in a clockwise direction each respective flange 40, 42. As shown in FIG. 6, each flange 40, 42 extends radially outward from an outer dose chamber cylindrical surface 44 of dose chamber 46 (shown in FIG. 1). Flanges 40 and 42 are each oriented in opposite directions. As shown in FIG. 2, flanges 40, 42 have proximal tapered surfaces that are positioned within respective complimentary tapered grooves 19, 21 and that are frictionally and abuttingly engaged to portions of arcuate sidewalls 20, 22. It should be understood that needle retention nut 14 may be configured to be attached to injection device 10 at locations other than outer dose chamber cylindrical surface 44.

As best shown in FIG. 5, needle offset nut 16 includes threads 48 positioned on a proximal portion of its cylindrical offset nut inner wall 50 that are configured to secure needle offset nut 16 to needle retention nut 14 by rotationally engaging in a counterclockwise direction with threads 52 positioned on cylindrical needle retention nut outer wall 54 of needle retention nut 14. Preferably, threads 48 and 52 are fine threads in order to reduce the effort required to either secure needle offset nut 16 to or remove it from needle retention nut 14.

Accordingly, as shown in FIG. 3, needle retention nut 14 is rotationally engaged to injection device 10 in a first rotational direction (i.e. —clockwise), and needle offset nut 16 is rotationally engaged to needle retention nut 14 in a second rotational direction that is opposite the first rotational direction (i.e.—counter-clockwise). As a result, needle offset nut 16 may be easily unscrewed and removed from needle retention nut 14 without the simultaneous and potentially undesirable unscrewing of needle retention nut 14 from injection device 10.

Figure 7:
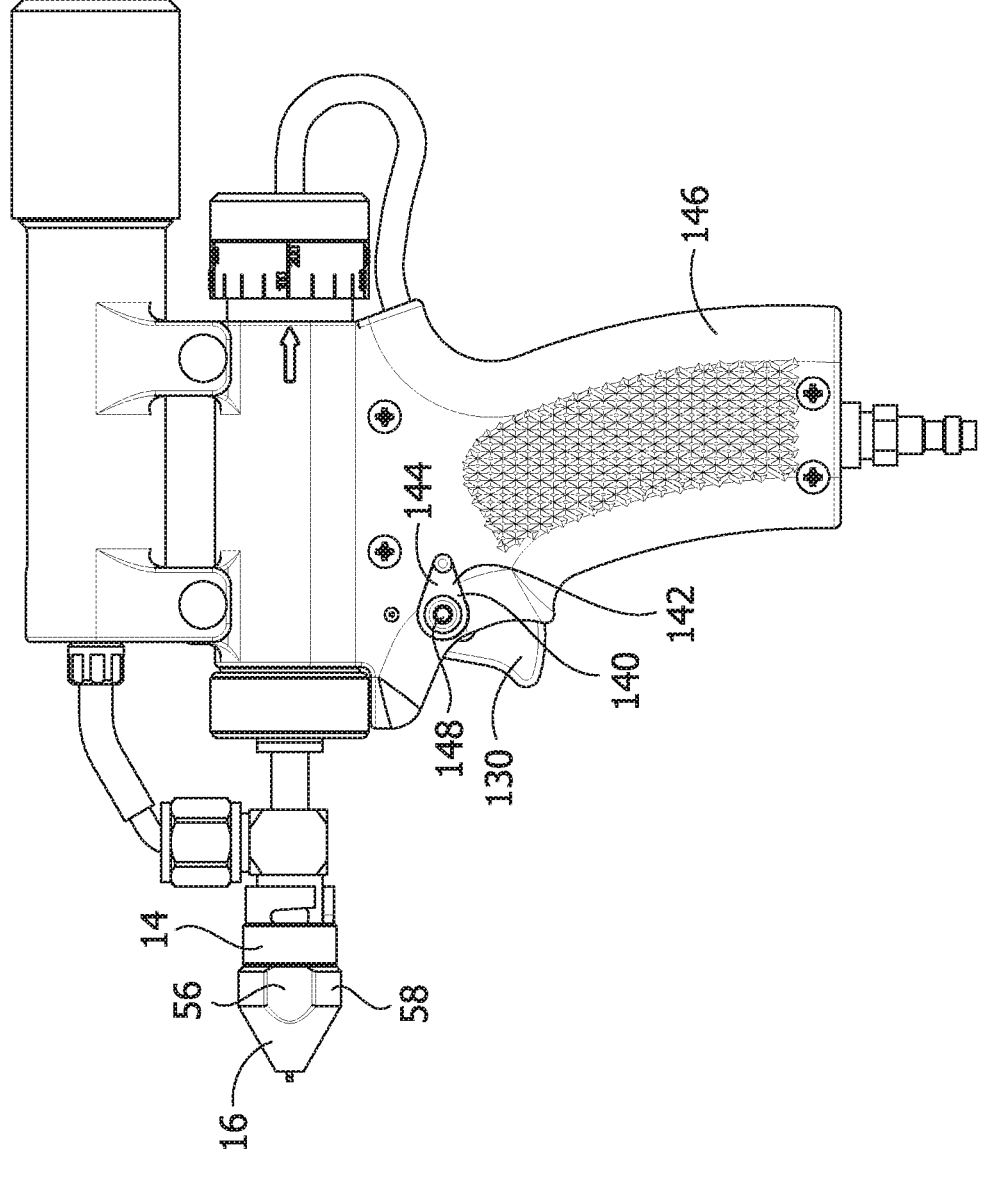
FIG. 7 is a side view of the injection device of FIG. 1 with the safety mechanism in the on position

It should be understood that the engagement of needle offset nut 16 to needle retention nut 14 and of needle retention nut 14 to injection device 10 may instead be achieved through the utilization of any suitable offset engagement mechanisms that allow needle retention nut 14 to be independently separated from needle offset nut 16 and injection device 10, including but not limited to threads, flange and flange engagement structures, pin-locks, ball-locks, key-locks, etc. It should also be understood that the outer surfaces of needle retention nut 14 and needle offset nut 16 may include structures, materials, or textures that make them easier to grip by a user's hand. For example, as shown in FIG. 7, one or more identical finger grips 56 may be positioned on an outer cylindrical wall 58 of needle offset nut 16, although only one finger grip 56 is shown.

As depicted in FIG. 4, needle retention nut 14 includes a retention nut opening 60 that is defined by needle retention nut inner cylindrical wall 24 and that is configured to receive a proximal portion of needle 18. As shown in FIG. 5, a proximal portion of needle 18 is positioned within retention nut opening 60. A distal portion of a cylindrical outer flange 62 of an integrally formed cylindrical base 64 of needle 18 is in abutting engagement with a proximal portion of cylindrical inner flange 66 of needle retention nut inner cylindrical wall 24 of needle retention nut 14. As shown in FIG. 1, needle 18, cylindrical base 64, and cylindrical dose chamber 46 of injection device 10 are in axial alignment, and a proximal portion of cylindrical base 64 is axially aligned and in abutting engagement with a distal end of dose chamber 46. Accordingly, needle 18 is removably secured to injection device 10 by needle retention nut 14. The exterior diameter of needle 18 is smaller than the diameter of retention nut opening 60. Although no specific size differential is required, the diameter of retention nut opening 60 is preferably oversized with respect to the diameter of needle 18 to enable easy insertion and removal of needle 18 to and from retention nut opening 60 and to allow movement out of axial alignment.

As shown in FIG. 5, needle offset nut 16 includes an offset nut channel 68 that is defined by a cylindrical offset nut channel inner wall 70 and that is configured to receive a distal portion of needle 18. As shown in FIG. 3, a distal portion of needle 18 is positioned within offset nut channel 68. The diameter of offset nut channel 68 is larger than the outer diameter of a distal portion of needle 18 preferably only slightly larger, and offset nut channel inner wall 70 is in abutting engagement with a sidewall 72 of a distal portion of needle 18 in order to provide support and improved rigidity to needle 18. In turn, needle 18 is less prone to offset or lateral movement which can lead to the misalignment/bending or breaking of needle 18.

As shown in FIG. 1, a tip portion 74 of needle 18 is positioned outside of offset nut channel 68. A leading planar surface 76 of needle offset nut 16 is configured to be positioned against a subject during an injection and serves as a stop point that sets the maximum penetration depth of needle 18 (i.e.—only tip portion 74 can penetrate a subject). Preferably, needle retention assembly 12 includes a plurality of interchangeable needle offset nuts 16 of varying heights h (see FIG. 3; plurality of needle offset nuts not shown) to enable a user to choose the length of the tip portion 74 of needle 18 that extends outside of offset nut channel 68 and thus the desired penetration depth of needle 18.

The present invention is also directed to a method of attaching a needle to an injection device. The method comprises: positioning a proximal portion of a needle within a retention nut opening of a needle retention nut; attaching the needle retention nut to an injection device; positioning an offset nut channel of a needle offset nut over a distal portion of the needle; and attaching the needle offset nut to the needle retention nut.

In certain embodiments, the attachment of a needle to an injector may be performed with injection device 10, needle retention assembly 12, and needle 18 according to the following exemplary method. Referring to FIG. 4, a proximal portion of needle 18 is positioned within retention nut opening 60 of needle retention nut 14. A distal portion of cylindrical base 64 is axially aligned with and positioned against a proximal portion of cylindrical inner flange 66 of retention nut opening inner wall 24 of needle retention nut 14. Referring to FIG. 6, alignment opening 28 of needle retention nut 14 is aligned with respective flange 40 of injection device 10, while on the opposite side opening 30 (not shown) is aligned with flange 42. Alignment openings 28, 30 are then positioned over respective flanges 40, 42 and needle retention nut 14 is rotated clockwise into the position shown in FIG. 2 in order that tapered flanges 40, 42 are positioned within respective tapered grooves 19, 21 and arcuate sidewalls 20, 22 and respective flanges 40, 42 frictionally and abuttingly engage one another. Accordingly needle retention nut 14 and injection device 10 are removably attached to one another and needle 18 is removably secured to a distal portion of dose chamber 46 (shown in FIG. 1). Next, as shown in FIG. 3, offset nut channel 68 of needle offset nut 16 is positioned over a distal portion of needle 18, offset nut channel inner wall 70 is positioned against sidewall 72 of a distal portion of needle 18, and needle offset nut 16 is rotated counterclockwise into the position shown in order to rotationally engage and removably attach needle offset nut 16 and needle retention nut 14 to one another.

The present invention is further directed to a method of removing a needle from an injection device. The method comprises: detaching a needle retention nut from an injection device; and removing the needle from a retention nut opening of the needle retention nut. In certain embodiments, the method further comprises detaching a needle offset nut from the needle retention nut, and optionally and preferably, this additional step may be performed prior to detaching the needle retention nut from the injection device.

Figure 8:
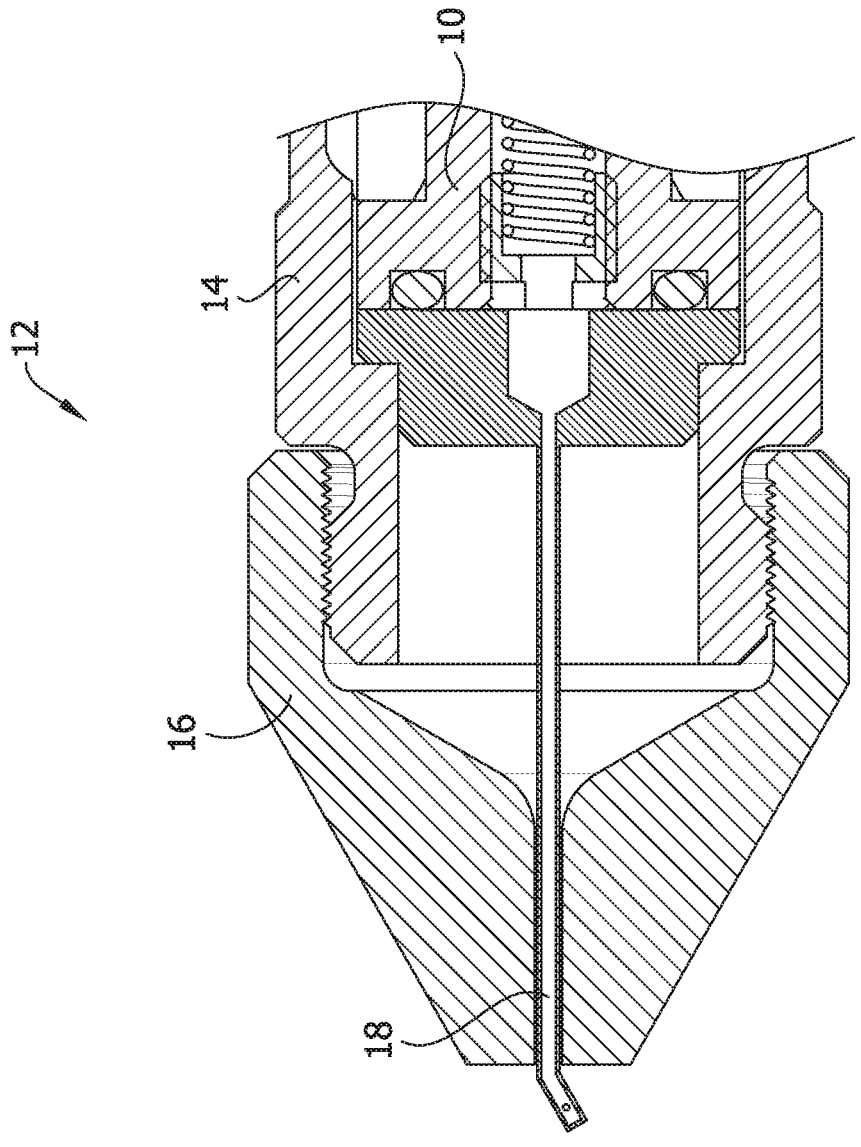
FIG. 8 is a partial cross-sectional view of the injection device of FIG. 1, showing the needle retention assembly with a bent needle.

In certain embodiments, the removal of a needle from an injection device may be performed with injection device 10, needle retention assembly 12, and needle 18 according to the following exemplary method. Referring to FIG. 3, needle offset nut 16 is rotated clockwise in order to rotationally disengage and detach needle offset nut 16 and needle retention nut 14 from one another. Next, offset nut channel inner wall 70 is taken out of contact with sidewall 72 of a distal portion of needle 18, and offset nut channel 68 of needle offset nut 16 is moved away from a distal portion of needle 18 to the position shown in FIG. 5. If needle 18 is bent, broken, and/or damaged as shown in FIG. 8, performing this step first allows a user to clear the bent, broken, and/or damaged portion of needle 18 without needle retention nut 14. As needle offset nut 16 is threadably detached from needle retention nut 14, the bent, broken, and/or damaged portion of needle 18 is simultaneously forced through offset nut opening 68. Once needle offset nut 16 is completely detached from needle retention nut 14, needle offset nut 16 is then more easily slidably removable over and past the bent, broken, and/or damaged portion of needle 18 in part because needle offset nut 16 is free to move out of axial alignment with needle retention nut 14. No tools are required; needle offset nut 16 can be removed by hand, and finger grips 56 allow for easier removability of needle offset nut 16. Next, with reference to FIG. 5, needle retention nut 14 is rotated counterclockwise to the orientation shown in FIG. 6 in order that arcuate sidewalls 20, 22 of radial grooves 19, 21 and respective flanges 40, 42 are disengaged from one another, and alignment openings 28, 30 are moved away from respective flanges 40, 42 in order to detach needle retention nut and injection device from one another. Needle 18 is then easily removed from oversized retention nut opening 60 of needle retention nut 14.

Returning to FIG. 1, another aspect of the present invention is directed to an injectate delivery system 78 for use with an injection device. Injectate delivery system 78 includes: an injectate holding compartment; a plunger slidably positionable within the injectate holding compartment forming a fluid tight seal with an inner wall of the injectate holding compartment; and a resilient member. When injectate holding compartment is attached to an injection device, it is in fluid communication with a dose chamber of the injection device. The resilient member is configured to apply continuous pressure to the plunger, thereby forcing an injectate from the injectate holding compartment to the dose chamber when the injectate holding compartment is attached to an injection device such that neither gravity nor negative pressure are required to the prime dose chamber.

Figure 9:
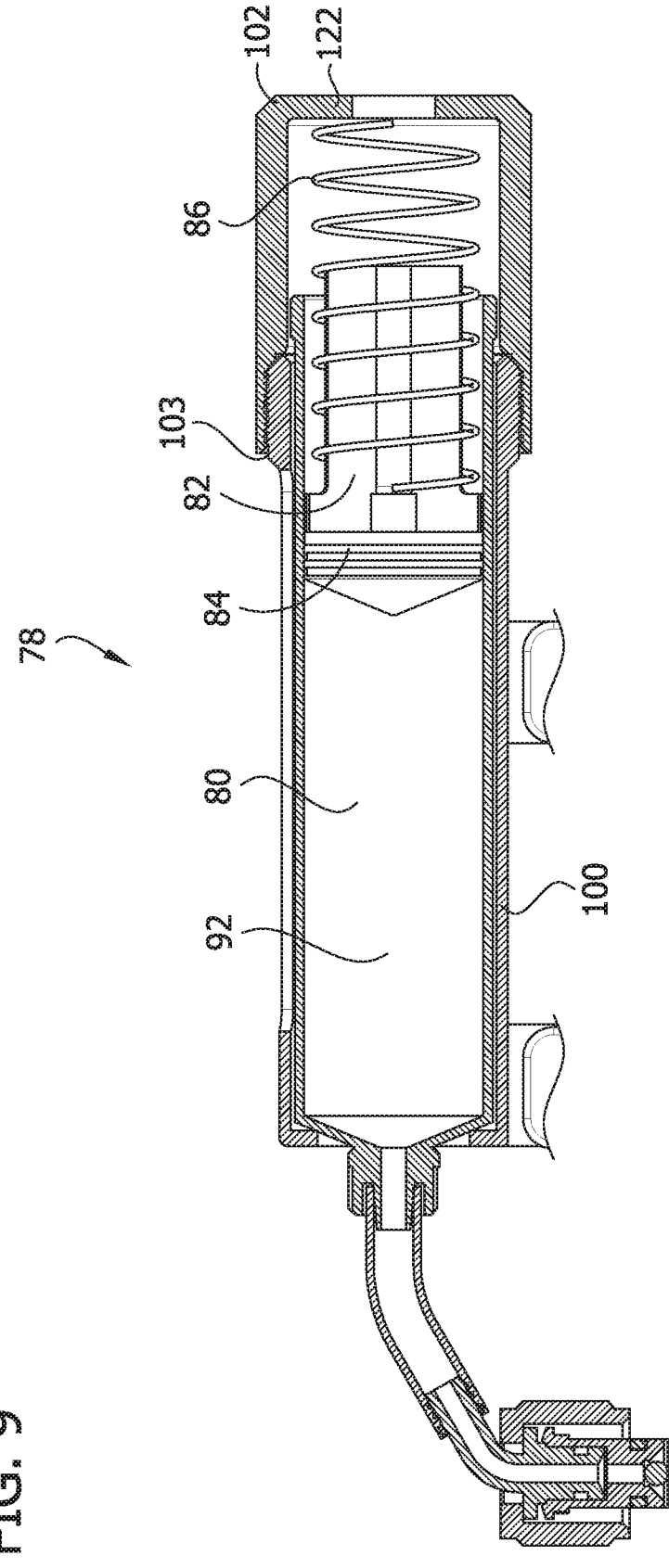
FIG. 9 is a sectional view of the injectate delivery system of the injection device of FIG. 1 in which the spring is in a compressed position.
Figure 10:
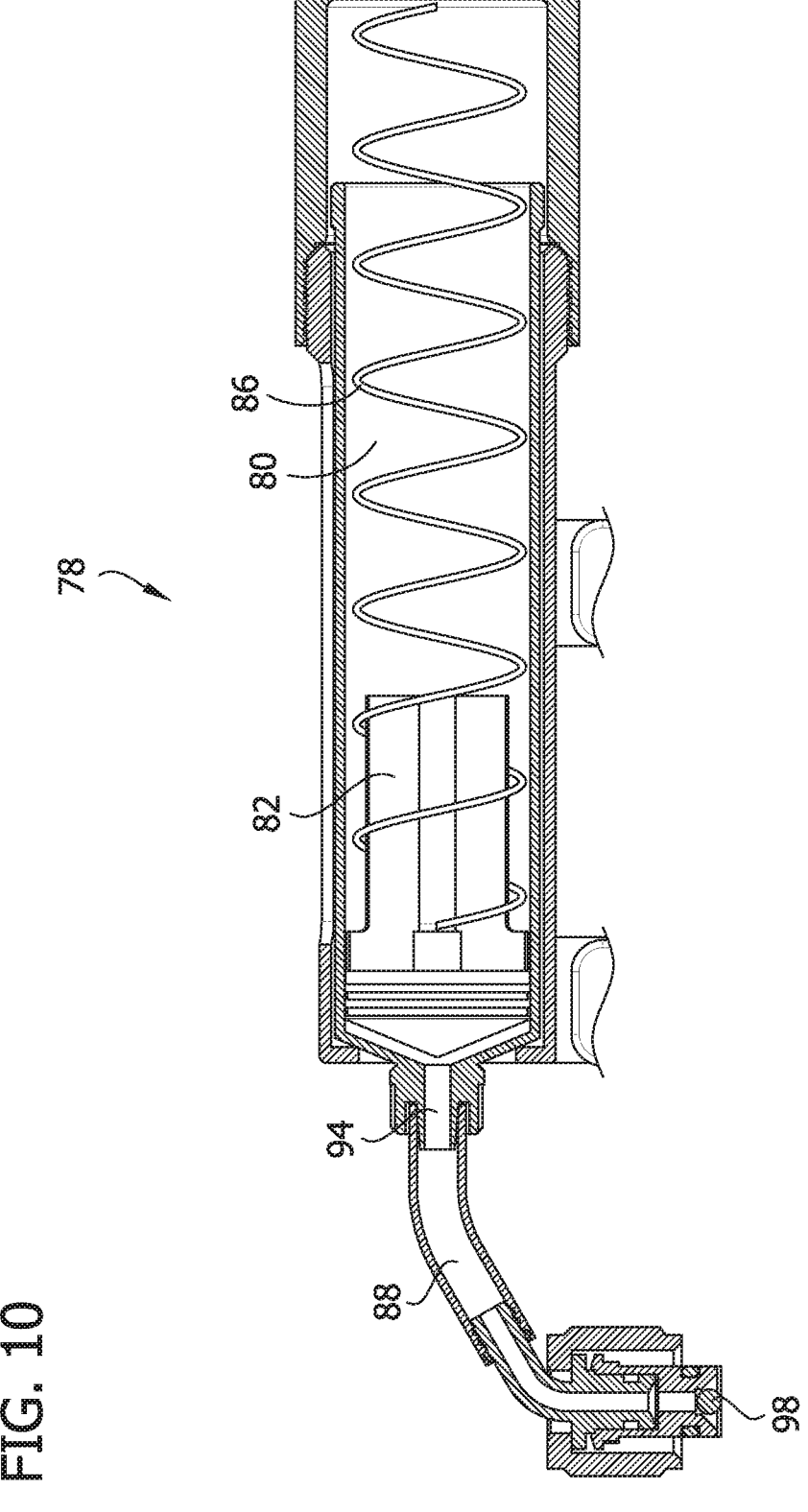
FIG. 10 is a sectional view of the injectate delivery system of the injection device of FIG. 1 in which the spring is in a partially uncompressed position.

As best shown in FIG. 6, injectate delivery system 78 includes cylindrical injectate holding compartment 80, cylindrical plunger 82 (which includes plunger seal 84), spring 86, inlet tube 88, and inlet valve assembly 90. Referring to FIG. 9, plunger 82 is slidably positioned within injectate holding compartment 80 and, plunger seal 84 forms a fluid tight seal with a cylindrical inner wall 92 of injectate holding compartment 80. As shown, plunger 82 is positioned at a proximal end of the injectate holding compartment 80 when spring 86 is compressed due to the presence of an injectate (not shown) in injectate holding compartment 80. FIG. 10 shows plunger 82 positioned at its most distal position at the distal end of injectate holding compartment 80 when spring 86 is partially uncompressed. Open tip 94 of injectate holding compartment 80 is in fluid communication with dose chamber opening 96 as shown in FIG. 6 via inlet tube 88. Referring to FIG. 1, inlet valve assembly 90, which includes ball valve 98 is configured to supply injectate to dose chamber 46 from injectate holding compartment 80 and to prevent injectate or air present within dose chamber 46 from flowing to injectate holding compartment 80. Ball valve 98 is always open and allows injectate from injectate holding compartment 80 to flow into the dose chamber 46. The ball valve 98 is closed only when there is back pressure on the ball of the ball valve 98 that results from distal movement of the injectate piston 99 of the injection device 10. Although injectate delivery system is shown with inlet valve assembly 90, it should be understood that any suitable inlet valve assembly (and any suitable valve) may be substituted, including but not limited to solenoid valves, shutter valves, membrane valves, etc.

Returning to FIG. 9, cylindrical injectate holding compartment 80 is slidably positioned within an opening in cylindrical barrel 100. A cylindrical barrel cap 102 is threadably attached to an outer surface 103 of cylindrical barrel 100 and is positioned over a proximal end of cylindrical barrel 100. As shown in FIG. 6, cylindrical barrel 100 is in turn attached to injection device 10 with identical bolts 104 that are each positioned within respective aligned openings 106, 108, 110, and 112; and 114, 116, 118, and an opening (not shown) corresponding to opening 112. It should be understood that cylindrical injectate holding compartment 80 may be attached to injection device 10 in any suitable manner as understood by one of ordinary skill in the art and need not necessarily be positioned within cylindrical barrel cap 102.

Referring back to FIG. 9, spring 86 is positioned between a proximal end of plunger 82 and a top 122 of barrel cap 102. Spring 86 is compressible and applies continuous pressure against plunger 82 such that any injectate present in injectate holding compartment 80 is forced to dose chamber 46 (shown in FIG. 1) in the event that dose chamber 46 is empty or partially empty. Accordingly, neither gravity nor negative pressure are required to prime dose chamber 46. It should be understood that although injectate delivery system 78 includes a spring 86, any suitable resilient member that is configured to apply continuous pressure to plunger 82 is within the scope of the invention.

In certain embodiments, as best shown in FIG. 1, plunger 82 includes a cylindrical bore that is defined by cylindrical bore sidewall 124 and that is configured to receive a threaded elongated tool (not shown). Preferably, as shown, bore sidewall 124 of plunger 82 includes threads 128 that are engageable with threads of a threaded elongated tool (not shown) in order that plunger 82 may be more easily moved distally within injectate holding compartment 80 by pulling the threaded tool when its threads are engaged with threads 128 in order to prime injectate holding compartment 80 with injectate.

Because injectate delivery system 78 does not rely upon the use of gravity and/or negative pressure, it is able to more consistently and more precisely deliver microscopic quantities of injectate (i.e.—as little as 20 μL) than injectate delivery systems of the prior art. For the same reason, the precision of injectate delivery system 78 is not impacted by its orientation during operation (i.e.—upside down, sideways, etc.).

The present invention is further directed to a method of using an injectate delivery system with an injection device. The method comprises the following steps: pressing a tip of a needle into a subject to be injected, wherein the needle is positioned for use in injection device; and injecting an injectate into the subject to be injected. The injectate is supplied to a dose chamber of the injection device from an injectate holding compartment of the injectate delivery system. A resilient member applies continuous pressure to a plunger of the injectate delivery system such that neither gravity nor negative pressure are required to prime the dose chamber. A movement of the plunger toward an end of the injectate holding compartment forces the injectate from the injectate holding compartment to the dose chamber.

In certain embodiments, the method of using an injectate delivery system may be performed with injection device 10, needle 18, and injectate delivery system 78 according to the following exemplary method. Referring to FIG. 1, a tip portion 74 of needle 18 is pressed into a subject to be injected, and an injectate (not shown) is injected into the subject. As described in more detail below, the injection is performed by depressing trigger 130, which in turn causes movement of injectate piston 132 within dose chamber 46 and toward its distal end. This movement of injectate piston 132 forces injectate present in dose chamber 46 through a central base opening 134 in a proximal end of cylindrical base 64 of needle 18, which is in fluid communication with longitudinal channel 136 (shown in FIG. 3) of needle 18. The injectate then flows into the subject through longitudinal channel 136 and orifices 138. The injectate is supplied to dose chamber 46 from injectate holding compartment 80. Spring 86 applies continuous pressure to plunger 82 such that neither gravity nor negative pressure are required to prime dose chamber 46, and plunger 82 moves toward a distal end of injectate holding compartment 80 in order to force the injectate from injectate holding compartment 80 to dose chamber 46. Once the injection is complete, injectate piston 132 moves within dose chamber 46 to return to its original position at a proximal end of dose chamber 46 as shown in FIG. 1. This rearward movement of injectate piston 132 creates a void space within dose chamber 46 that is immediately filled with more injectate that is supplied from injectate holding compartment 80 and through inlet tube 88 and inlet valve assembly 90. In certain embodiments, the method further comprises selecting the needle retention nut 16 that will control the desired injection depth. In some such embodiments, the subject is a plant, such as a grapevine, and the needle retention nut 16 is selected to result in an injection in the target xylem layer.

The present invention is also directed to a needle 18 for use with an injection device 10. Needle 18 has a sidewall defining a longitudinal channel. Needle 18 includes at least two orifices in a sidewall of needle 18 and does not include an orifice at a tip of needle 18.

Figure 11:
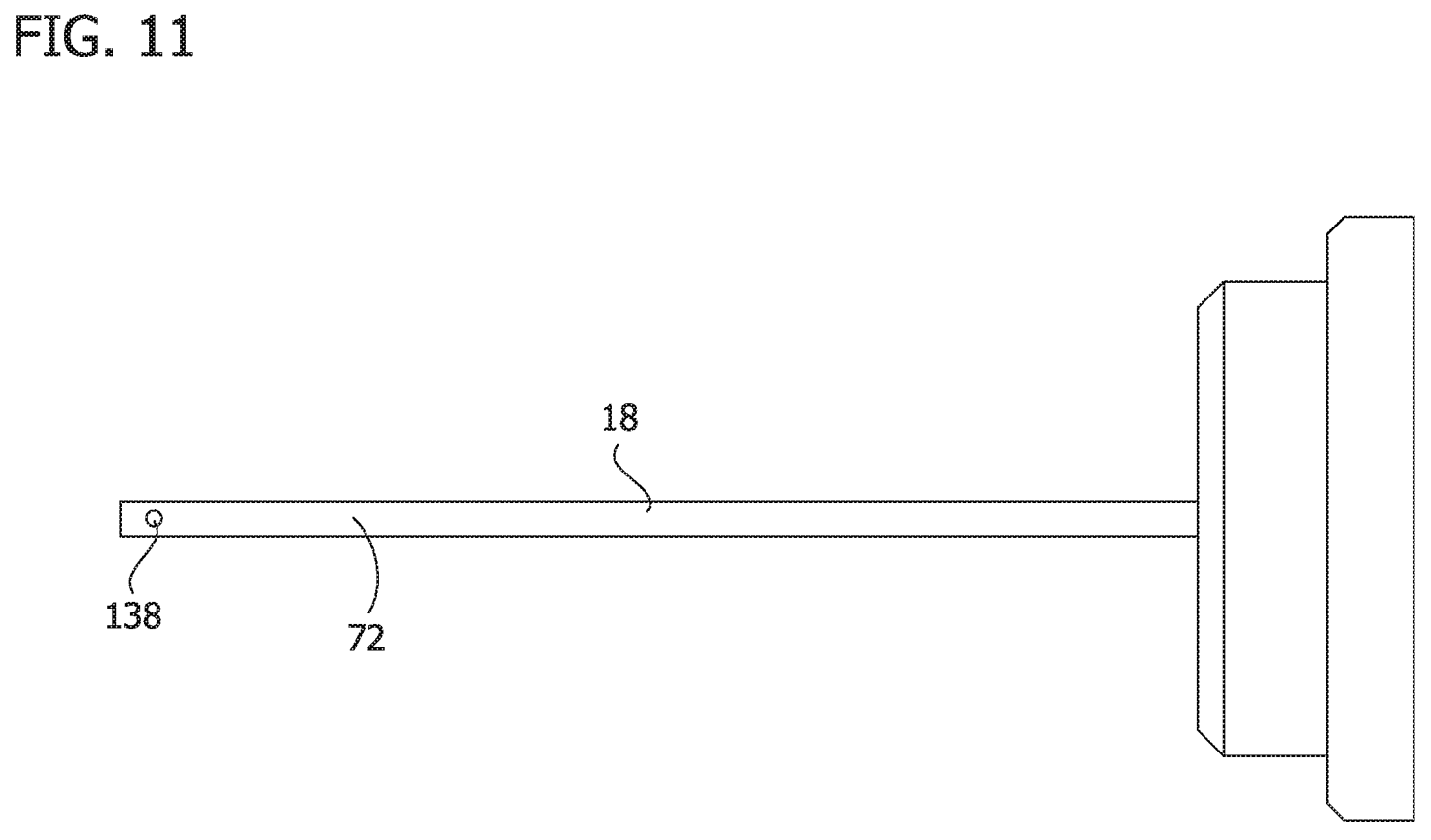

Turning to FIGS. 3 and 11, needle 18 includes two identical orifices 138 positioned on opposing surfaces of sidewall 72—no orifice is included on a tip of needle 18. Referring to FIG. 3, when needle 18 is attached to injection device 10 and is used to perform an injection, orifices 138 are positioned distal to offset nut channel inner wall 70, and injectate injected into a subject is forced to flow through orifices 138. The inclusion of multiple smaller orifices 138—as opposed to a single larger orifice on a tip of needle 18—improves the rigidity of needle 18 during an injection. Additionally, the positioning of orifices 138 on sidewall 72 of needle 18—as opposed to a single orifice positioned at a tip of needle 18—both reduces the risk that needle 18 will become plugged during an injection and allows the injectate to be forced laterally into a target layer of a subject when orifices 138 are positioned within the target layer. For example, needle 18 can be used to target a xylem layer of a grape vine. As described above, needle retention nuts 16 of varying height h can be used in order to inject at a specific depth, for example the depth of the xylem layer.

Another aspect of the present invention is directed to a safety mechanism 140 for use with an injection device. The safety mechanism 140 includes a dual switch that itself includes two switch elements. Each switch element is positionable on opposing sides of a handle of an injection device. The dual switch is movable between an on and an off position, and movement of a switch element on one side of the dual switch automatically moves the switch element on the opposite side of the handle when the switch element is positioned on the two opposing sides of the handle of an injection device. Safety mechanism 140 is operable by either the left or right hand of a user. Preferably, at least one of the switch elements further includes a depressible button. The dual switch is movable between the on and the off positions by simultaneously depressing the button and moving either switch element between the on and the off position.

As shown in FIG. 2, safety mechanism 140 includes a dual switch 142 with identical switch elements 144 positioned on each side of handle 146 of injection device 10 (opposite side not shown). Dual switch 142 is moveable between an on position depicted in FIG. 2 and an off position depicted in FIG. 7, and movement of one switch element 144 positioned on one side of dual switch 142 automatically moves a second switch element 144 positioned on the opposite side of dual switch 142. If dual switch 142 is in the off position, trigger 130 is not movable, and as a result, injection device 10 is not capable of performing injections. If dual switch is in the on position, trigger 130 is movable, and as a result, injection device 10 is capable of performing injections. One switch element 144 includes a depressible button 148. Depressing the button 148 inward and toward handle 146 allows angular simultaneous movement of both switch elements 144. While the button 148 is depressed, the switch elements 144 are rotatable between the on and off positions. A user may rotate dual switch 142 using either switch element 144 with either the left or right hand.

It should be understood that the needle retention assembly 12, injectate delivery system 78, multi-orifice needle 18, and safety mechanism 140 of the present invention may be used with virtually any injection device that is configured for use with a needle and may be attached to an injection device by various mechanisms suitable for the specific injection device, as will be readily understood by one of ordinary skill in the art. Suitable injection devices include, but are not limited to, syringes alone or in combination with other components/mechanisms that facilitate injections. It should further be understood that the needle retention assembly, injectate delivery system, multi-orifice needle, and safety mechanism of the present invention may be used with an injection device in conjunction with injecting animals, humans, or plants. The needle retention assembly of the present invention is well suited for use with an injection device to inject subjects with tough or woody exteriors or layers in view of the support it is configured to provide to a needle and in view of its functionality in replacing bent needles. Similarly, the needle of the present invention is well suited for use with an injection device to inject subjects with tough or woody exteriors or layers in view of its improved rigidity.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

I claim:

1. A needle retention assembly for use with an injection device comprising:
   a needle retention nut; and
   a needle offset nut;
   wherein the needle retention nut is configured to removably attach to the injection device and to removably secure a needle to the injection device, and wherein the needle offset nut is configured to removably attach to the needle retention nut and to provide support to the needle;
   wherein the needle offset nut comprises an offset nut channel for receiving a distal portion of the needle;
   wherein the offset nut channel is defined by an offset nut channel inner wall;

wherein when the needle offset nut is removably attached to the needle retention nut, the distal portion of the needle is positioned within the offset nut channel;
   wherein a diameter of the offset nut channel is larger than an outer diameter of the distal portion of the needle; and
   wherein the offset nut channel inner wall of the offset nut channel is in abutting engagement with a side wall of a distal portion of the needle when the needle is removably secured to the injection device by the needle retention nut.

2. The needle retention assembly of claim 1, wherein the needle retention nut and the needle offset comprise an offset engagement mechanism that allows the needle retention nut to be independently separated from the needle offset nut and the injection device.

3. The needle retention assembly of claim 2, wherein the offset engagement mechanism is selected from the group consisting of threads, flange and flange engagement structures, pin-locks, ball-locks, key-locks, and combinations thereof.

4. The needle retention assembly of claim 1, wherein the needle retention nut is removably attachable to the injection device via rotational engagement.

5. The needle retention assembly of claim 1, wherein the needle offset nut is removably attachable to the needle retention nut via rotational engagement.

6. The needle retention assembly of claim 1, wherein the needle retention nut is removably attachable to the injection device via rotational engagement in a first rotational direction, and wherein the needle offset nut is removably attachable to the needle retention nut via rotational engagement in a second rotational direction that is opposite the first rotational direction.

7. The needle retention assembly of claim 1, wherein the needle retention nut comprises a retention nut opening for receiving a proximal portion of the needle, wherein the needle retention nut opening is defined by a retention nut opening inner wall, wherein when the needle retention nut is removably attached to the injection device and the needle is removably secured to the injection device, wherein the proximal portion of the needle is positioned within the retention nut opening, and wherein a diameter of the proximal portion of the needle is smaller than a diameter of the retention nut opening.

8. A method of attaching the needle to the injection device with the needle retention assembly of claim 1, comprising:
   positioning the proximal portion of the needle within the retention nut opening of the needle retention nut;
   attaching the needle retention nut to the injection device;
   positioning the offset nut channel of the needle offset nut over a distal portion of the needle; and
   attaching the needle offset nut to the needle retention nut.

9. A method of removing the needle from the injection device that includes the needle retention assembly of claim 1, comprising:
   detaching the needle retention nut from the injection device; and
   removing the needle from the retention nut opening of the needle retention nut.

10. The method of claim 9, further comprising detaching the needle offset nut from the needle retention nut.

11. The method of claim 9, wherein the needle offset nut is detached from the needle retention nut prior to detaching the needle retention nut from the injection device.

12. An injection device comprising the needle retention assembly of claim 1.

\* \* \* \* \*